(12) United States Patent
Beymer et al.

(10) Patent No.: US 11,357,435 B2
(45) Date of Patent: Jun. 14, 2022

(54) AUTOMATIC EXTRACTION OF DISEASE-SPECIFIC FEATURES FROM DOPPLER IMAGES

(71) Applicant: International Business Machines Corporation, Armonk, NY (US)

(72) Inventors: David J. Beymer, San Jose, CA (US); Mehdi Moradi, San Jose, CA (US); Mohammadreza Negahdar, San Jose, CA (US); Nripesh Parajuli, New Haven, CT (US); Tanveer F. Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 556 days.

(21) Appl. No.: 16/412,533

(22) Filed: May 15, 2019

(65) Prior Publication Data
US 2019/0261880 A1 Aug. 29, 2019

Related U.S. Application Data

(63) Continuation of application No. 15/295,389, filed on Oct. 17, 2016, now Pat. No. 10,362,949.

(51) Int. Cl.
*A61B 8/00* (2006.01)
*A61B 5/316* (2021.01)
(Continued)

(52) U.S. Cl.
CPC .............. *A61B 5/316* (2021.01); *A61B 5/318* (2021.01); *A61B 5/7264* (2013.01);
(Continued)

(58) Field of Classification Search
None
See application file for complete search history.

(56) References Cited

U.S. PATENT DOCUMENTS

8,295,569 B2   10/2012   Park et al.
8,315,450 B2   11/2012   Quigley
(Continued)

OTHER PUBLICATIONS

Baumgartner et al. (Echocardiographic assessment of valve stenosis: EAE/ASE recommendations for clinical practice) (Year: 2009).*
(Continued)

*Primary Examiner* — Joel F Brutus
(74) *Attorney, Agent, or Firm* — Schmeiser, Olsen & Watts, LLP; Randall Bluestone

(57) ABSTRACT

An automatic extraction of disease-specific features from Doppler images to help diagnose valvular diseases is provided. The method includes the steps of obtaining a raw Doppler image from a series of images of an echocardiogram, isolating a region of interest from the raw Doppler image, the region of interest including a Doppler image and an ECG signal, and depicting at least one heart cycle, determining a velocity envelope of the Doppler image in the region of interest, extracting the ECG signal to synchronize the ECG signal with the Doppler image over the at least one heart cycle, within the region of interest, calculating a value of a clinical feature based on the extracted ECG signal synchronized with the velocity envelope, and comparing the value of the clinical feature with clinical guidelines associated with the clinical feature to determine a diagnosis of a disease.

18 Claims, 20 Drawing Sheets

(51) Int. Cl.
  *A61B 5/00* (2006.01)
  *A61B 8/08* (2006.01)
  *A61B 5/318* (2021.01)
  *A61B 5/02* (2006.01)

(52) U.S. Cl.
  CPC .......... *A61B 5/7425* (2013.01); *A61B 8/0883* (2013.01); *A61B 8/486* (2013.01); *A61B 8/488* (2013.01); *A61B 5/02028* (2013.01)

(56) References Cited

U.S. PATENT DOCUMENTS

| | | | |
|---|---|---|---|
| 8,355,548 | B2 | 1/2013 | Kovacs, Jr. et al. |
| 8,712,122 | B2 | 4/2014 | Syeda-Mahmood et al. |
| 9,135,699 | B2 | 9/2015 | Ralovich et al. |
| 9,167,974 | B2 | 10/2015 | Taylor |
| 2009/0226058 | A1* | 9/2009 | Li .................... G06T 7/149 382/128 |
| 2011/0262018 | A1 | 10/2011 | Kumar et al. |
| 2012/0020563 | A1* | 1/2012 | Amir .................. G06K 9/346 382/182 |
| 2013/0085404 | A1* | 4/2013 | de Melis ........... A61B 5/0245 600/513 |
| 2014/0276011 | A1* | 9/2014 | Schmitt ........... A61B 5/02007 600/425 |
| 2015/0170055 | A1* | 6/2015 | Beymer .............. G06N 20/00 706/12 |
| 2015/0351703 | A1 | 12/2015 | Phillips et al. |
| 2018/0103914 | A1 | 4/2018 | Beymer et al. |

OTHER PUBLICATIONS

Negahdar et al., Automatic Extraction of Disease-Specific Features From Doppler Images, IBM Research-Almaden, San Jose, CA, USA, Department of Electrical Engineering, Yale University, New Haven, CT, USA, 4 pages.

Authors et. al.: IBM, Content-similarity guided decision support in healthcare, Original Publication Date: Nov. 6, 2008, IP.com No. IPCOM000176158D, IP.com Electronic Publication Date: Nov. 6, 2008, 14 pages.

Baumgartner et al., Echocardiographic assessment of valve stenosis: EAE/ASE recommendations for clinical practice, European Journal of Echocardiography (2009) 10, 1-25, doi:10.1093/ejechocard/jen303, 25 pages.

T.Syeda-Mahmood et al., Shape-based Similarity Retrieval of Doppler Images for Clinical Decision Support, IBM Almaden Research Center, 650 Harry Road, University of Maryland, College Park, Retrieved from Internet: http://www.almaden.ibm.com/cs/projects/aalim, 8 pages.

Tanveer Syeda-Mahmood et al., Disease-Specific Extraction of Text from Cardiac Echo Videos for Decision Support, 2009 10th International Conference on Document Analysis and Recognition, IBM Almaden Research Center 650 Harry Road, San Jose, CA 95120 USA, 978-0-7695-3725-2/09 $25.00 © 2009 IEEE DOI 10.1109/CDAR.2009.269 pp. 1290-1294.

Beymer, et al., Automatic Estimation of Left Ventricular Dysfunction from Echocardiogram Videos, 978-1-4244-3993-5/09, copyright 2009 IEEE, pp. 164-171.

Office Action (dated Sep. 24, 2018) for U.S. Appl. No. 15/295,389, filed Oct. 17, 2016.

Amendment (dated Jan. 24, 2019) for U.S. Appl. No. 15/295,389, filed Oct. 17, 2016.

Notice of Allowance (dated Feb. 21, 2019) for U.S. Appl. No. 15/295,389, filed Oct. 17, 2016.

* cited by examiner

| VALVE STENOSIS | | | | | | |
|---|---|---|---|---|---|---|
| BSA 2.13 m² | Ht. 180.3 cm | Wt. 92.988 kg | | Years | BP | |

Aortic Valve — Aortic Doppler

| | | | | | |
|---|---|---|---|---|---|
| AoV Vmax | 2.16 | m/sec | AoV Pk Grad | 18.7 | mmHg |
| AoV VTI | 0.320 | m | AoV Mn Grad | 8.5 | mmHg |
| AoV AT | 8 | msec | AoV AT/ET | 0.03 | |
| AoV ET | 234 | msec | | | |

Aortic Valve — AoV Continuity Equation

| | AoV | LVOT | | | | |
|---|---|---|---|---|---|---|
| VTI | 0.320 | 0.223 | m | AoV Area, VTI | 2.26 | cm² |
| Vmax | 2.16 | 1.38 | m/sec | AoV Area, Vmax | 2.06 | cm² |
| Vmean | 1.380 | 0.863 | m/sec | AoV Area, Vmean | 2.02 | cm² |
| LVOT Diam | 2.03 | | cm | AoV Area/BSA, VTI | 1.06 | cm²/m² |
| LVOT Area | 3.24 | | cm² | AoV Area/BSA, Vmax | 0.97 | cm²/m² |
| | | | | AoV Area/BSA, Vmean | 0.95 | cm²/m² |

Mitral Valve — MV Doppler

| | | | | | |
|---|---|---|---|---|---|
| MV Peak E | 1.40 | m/sec | MV Mn Grad | 5.2 | mmHg |
| MV Peak A | 1.40 | m/sec | Mv P½T | 82 | msec |
| MV VTI, leaflet tips | 0.340 | m | MV Area, P½T | 2.67 | cm² |
| | | | MV DT | 284 | msec |

[ Page Up ]  [ Page Down ]  [ Image ]  [ Expand ]

AUTOMATIC EXTRACTION OF DISEASE-SPECIFIC FEATURES FROM DOPPLER IMAGES

This application is a continuation application claiming priority to Ser. No. 15/295,389, filed Oct. 17, 2016, now U.S. Pat. No. 10,362,494, issued Jul. 30, 2019.

TECHNICAL FIELD

The present invention relates to systems and methods for automatic extraction of disease-specific features from Doppler images to help diagnose diseases of the valves.

BACKGROUND

Flow Doppler imaging is widely used by clinicians to detect diseases of the valves, such as aortic regurgitation, aortic stenosis, mitral regurgitation, and mitral stenosis. In particular, continuous wave Doppler (CW) mode scan is routinely done during echocardiography, and images showing the Doppler signal tracings are intermixed with other scan modes in an echocardiographic video recording. Traditionally, echocardiographers have manually traced velocity envelopes to extract measurements, such as decay time, pressure gradient, pressure half-time, and velocity time integral, which are then matched to normal and abnormal values based on clinical guidelines. However, the measurements made by echocardiographers can show considerable variability for measurement of ejection fraction. Further, although there are over 146 measurements that can be made during echocardiography, only a subset of them are based on what diseases are anticipated for the patients.

SUMMARY

An embodiment of the present invention relates to a method, and associated computer system and computer program product, for automatically detecting disease-specific features using Doppler images. A raw Doppler image from a series of images of an echocardiogram is obtained. A region of interest from the raw Doppler image is isolated, the region of interest including a Doppler image and an ECG signal, and depicting at least one heart cycle. A velocity envelope of the Doppler image in the region of interest is determined, and the ECG signal is extracted to synchronize the ECG signal with the Doppler image over the at least one heart cycle, within the region of interest. A value of a clinical feature is calculated based on the extracted ECG signal synchronized with the velocity envelope, and the value of the clinical feature is compared with clinical guidelines associated with the clinical feature to determine a diagnosis of a disease.

BRIEF DESCRIPTION OF THE DRAWINGS

FIG. 1 depicts a sample of text-only echocardiogram page.

DETAILED DESCRIPTION

Typically, an echocardiographer is asked to make certain measurements to be made based on a suspected disease. In the case of coincidental findings, the echocardiographers may often fail to make all the necessary measurements. An automatic method for systematically making all those measurements would not only reduce the examination time of the technician, but also give rise to consistent measurements that can then be verified by the cardiologists. This would also help uncover missing diagnosis or coincidental findings.

Accordingly, a fully automatic method of deriving the measurements is provided herein. Embodiments of the method may relate to a specific class of aortic valve diseases, including aortic stenosis. Further embodiments of the present method may be utilized to detect and/or diagnose any valvular disease. To compare a performance of the present method with measurements made by echocardiographers, the echocardiograms may be analyzed retrospectively and extract the measurements made by echocardiographers that are often captured as text-only screens in echocardiograms as shown in FIG. 1. The measurements may be derived directly by automatically analyzing Doppler envelopes. Specifically, a robust pipeline of analytics may be developed that use multiple sources of information found in Doppler images. In particular, an enhanced detector for ECG traces in Doppler envelopes to derive periodicity information may be developed. Next, an enhanced envelop detector may augment traditional Doppler envelop tracing with technician-generated extrapolations in cases of an ambiguous Doppler signal. Unlike previous approaches to Doppler shape pattern detection that focused only on capturing an overall shape of the Doppler envelope, the present method also produces a clinical measurement(s), such as peak velocity (Vmax) and mean pressure gradient (MPG), and map to clinical guidelines to derive additional diagnosis labels.

Figure 2:
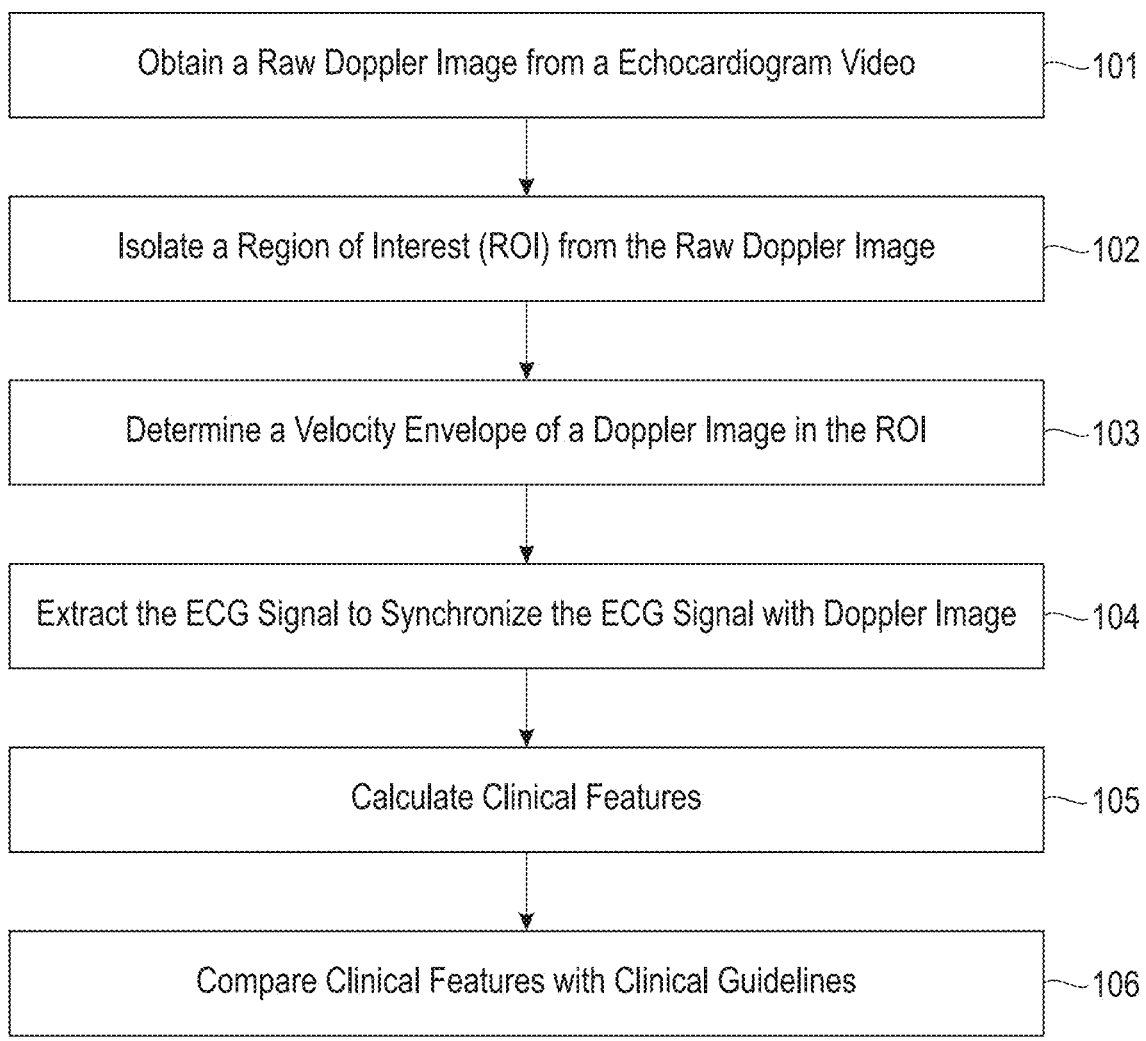
FIG. 2 depicts a flow chart of a method for automatically detecting disease-specific features using Doppler images, in accordance with embodiments of the present invention.

Flow Doppler imaging, recorded during an echocardiographic exam, is widely used by clinicians to diagnose valvular diseases. CW Doppler imaging has become popular due to a high temporal and velocity resolution as CW Doppler imaging avoids aliasing through continuous scanning. Thus, clinical features may be extracted for detecting a valvular disease, such as aortic stenosis (AS) from CW Doppler images FIG. 2 depicts a flow diagram of an exemplary method for automatic extraction of disease-specific features from Doppler images 100, in accordance with embodiments of the present invention. Embodiments of the method for automatic extraction of disease-specific features from Doppler images 100 may include the following steps: obtaining a raw Doppler image from a series of images of an echocardiogram, isolating a region of interest from the raw Doppler image, the region of interest including a Doppler image and an ECG signal, and depicting at least one heart cycle, determining a velocity envelope of the Doppler image in the region of interest, extracting the ECG signal to synchronize the ECG signal with the Doppler image over the at least one heart cycle, within the region of interest, calculating a value of a clinical feature based on the extracted ECG signal synchronized with the velocity envelope that is superimposed on the Doppler image; and comparing the value of the clinical feature with clinical guidelines associated with the clinical feature to determine a diagnosis of a disease.

Figure 3:
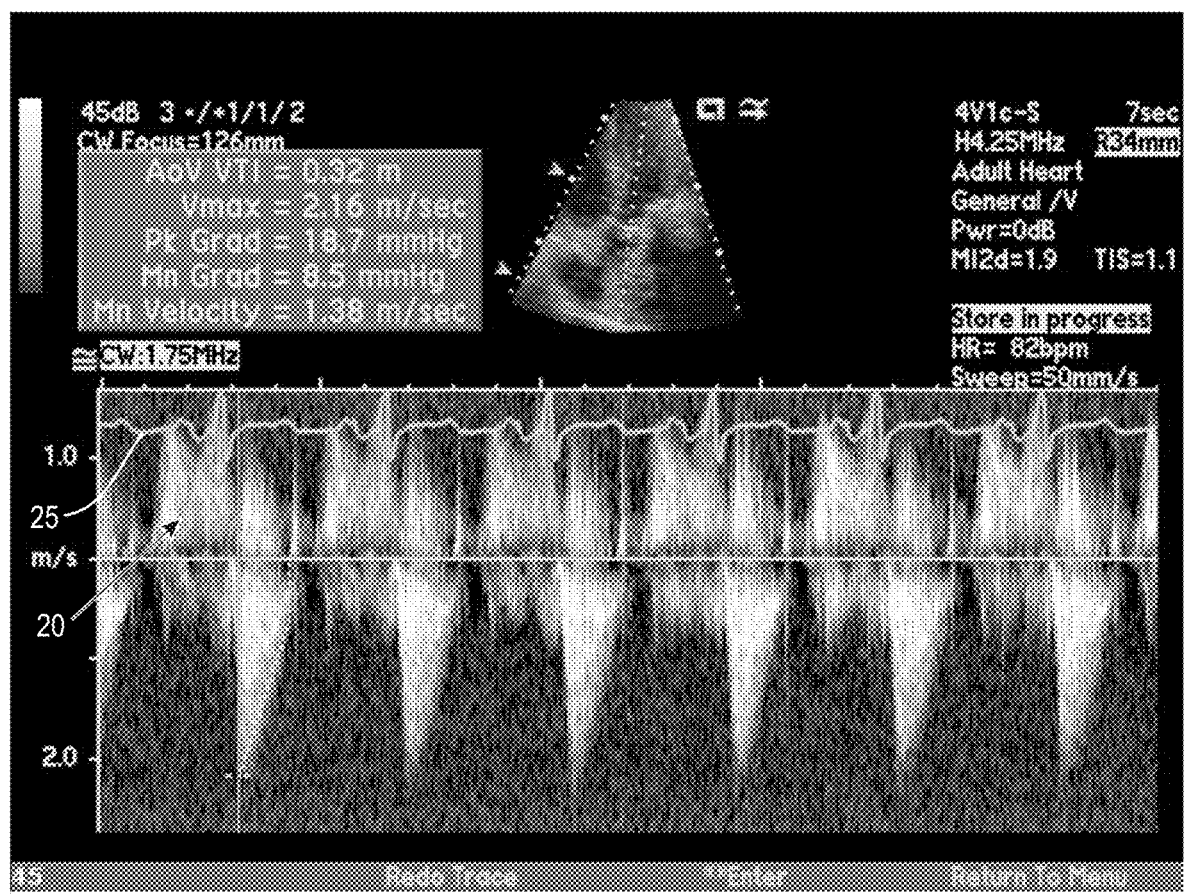
FIG. 3 depicts a raw Doppler image obtained from a series of images of an echocardiogram, in accordance with embodiments of the present invention.

Step 101 obtains a raw Doppler image from a series of images of an echocardiogram. FIG. 3 depicts a raw Doppler image, in accordance with embodiments of the invention. For instance, a patient may undergo an echocardiogram using various echocardiogram machines (e.g. Siemens Sequoia, Siemens Cypress, and the like), which may output an echocardiogram video, or a series of images or frames. The series of images from the echocardiogram may include various modes, such as two-dimensional imaging, M-mode imaging, and Doppler imaging, and the like. Embodiments of the present method may categorize the series of images to obtain a raw Doppler image, which can include CW Doppler or PW Doppler. The series of images may be categorized using an optical character recognition engine and/or machine learning to distinguish and categorize the series of images to isolate and obtain a raw Doppler image. In an exemplary embodiment, the raw Doppler image may be obtained by building templates from echocardiogram frames received from an echocardiogram machine that capture an expected position and a size of the Doppler regions in an echocardiogram video frame. By applying the templates, all Doppler frames, such as CW and PW Doppler, in an echocardiogram video may be isolated. To distinguish CW Doppler frames from PW and other Doppler image types, an optical character recognition engine (e.g. Tesseract) may be utilized to look for appropriate keywords such as 'CW' or 'PW'. In further embodiments, machine learning may be incorporated to categorize the series of images to eventually obtain a raw Doppler image. The raw Doppler image may include a Doppler image 20 and an ECG signal 25, as shown in FIG. 3, but also include unwanted information, text, images, etc.

Figure 4:
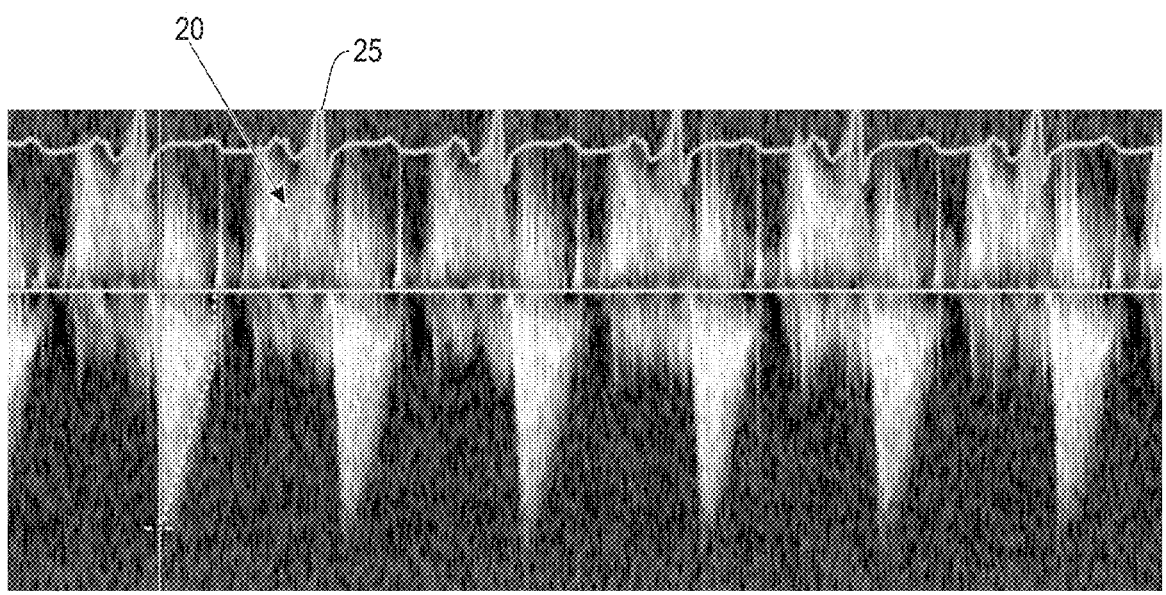
FIG. 4 depicts a region of interest extracted from the raw Doppler image of FIG. 3, in accordance with embodiments of the present invention.

Step 102 extracts or isolates a region of interest from the raw Doppler image obtained by step 101 to remove unwanted text, information, images, etc. For example, the raw Doppler image may include overlaid text, an anatomic image, various information and indicia, which is a result of the echocardiogram. In other words, the Doppler image of interest may be overlaid or covered in text, moving heart regions, or may include unwanted noise and or information. To separate the Doppler image frames from other frames that depict the moving heart regions, rectangular templates may be created to capture the Doppler region. Further, the region of interest may be isolated by detecting and removing the straight axis lines, peaks, and equally spaced vertical strikes of the bounding box of the raw Doppler image. The axes that are associated with text or form portions of unwanted information/text may be distinguished from an axis relating to the Doppler image, and then may be removed. As a result, the region of interest may be extracted, isolated, created, etc., which includes the Doppler velocity profile, or the Doppler image 20, and the ECG signal 25, as shown in FIG. 4.

Figure 5A:
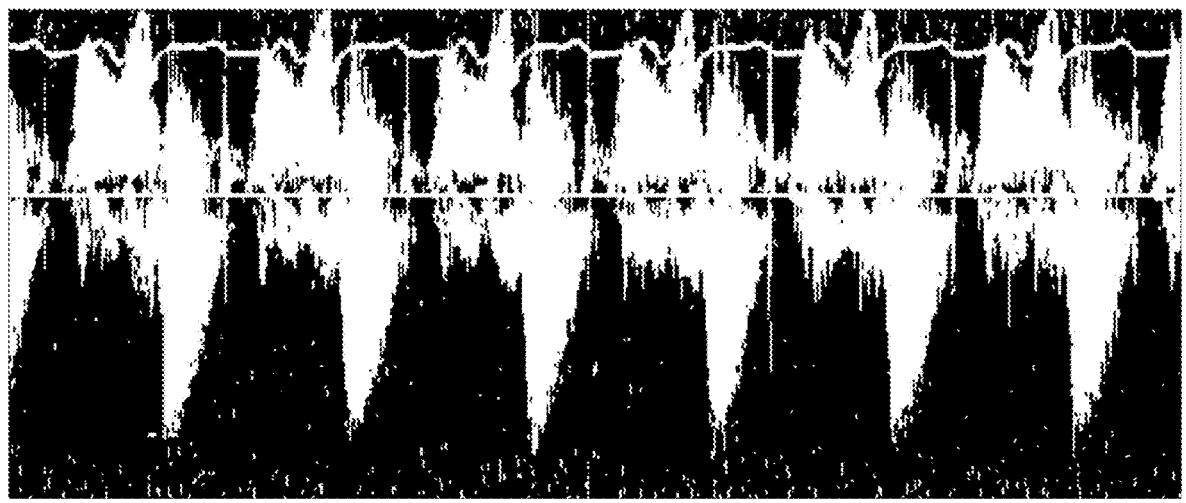
FIG. 5A depicts a Doppler image after a foreground/background technique has been applied, in accordance with embodiments of the present invention.
Figure 5B:
FIG. 5B depicts a Doppler image after a largest region of the Doppler image has been retained from the Doppler image of FIG. 5A, in accordance with embodiments of the present invention.
Figure 5C:
FIG. 5C depicts a Doppler image after dilation to fill up holes in the Doppler image of FIG. 5B, in accordance with embodiments of the present invention.
Figure 5D:
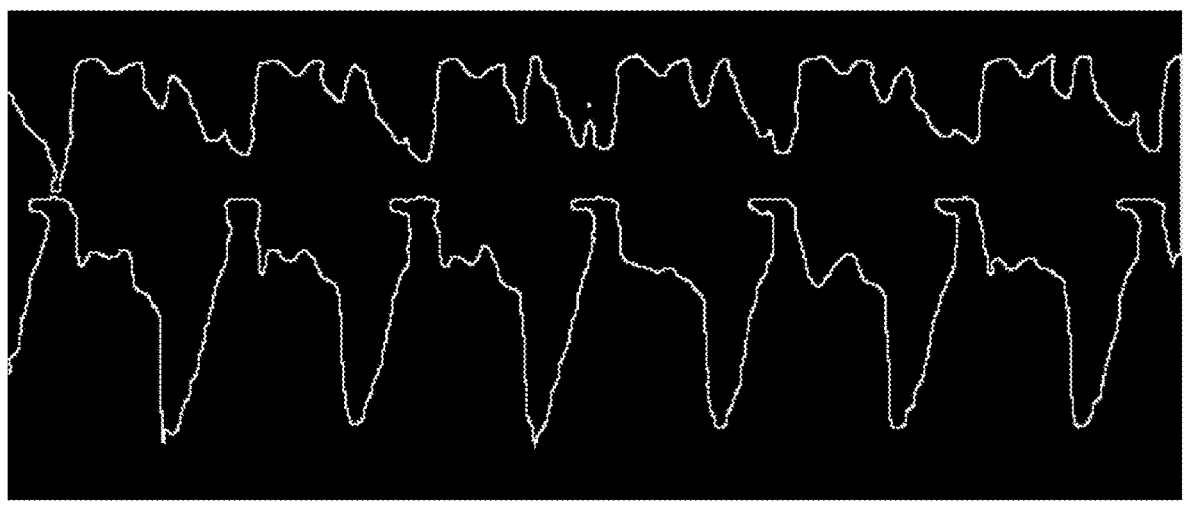
FIG. 5D depicts a velocity profile traced from the Doppler image of FIG. 5C, in accordance with embodiments of the present invention.

Referring still to FIG. 2 and with additional reference to FIGS. 5A-5D, step 203 determines a velocity envelope of the Doppler image 20 in the region of interest. For example, determining a velocity envelope of the Doppler image 20 may include tracing a Doppler image located within a region of interest to extract an upper velocity envelope 26 and a lower velocity envelope 27 of the Doppler image 20. The trace of the Doppler velocity profile, or Doppler image 20, may be needed for the calculation of the clinical features. To extract the trace of the Doppler image 20, a foreground/background separation may be applied with Otsu's thresholding to highlight the Doppler velocity profiles within the region of interest, as shown in FIG. 5A. Otsu's thresholding algorithm may calculate an optimum threshold separating the foreground and background classes so that the foreground and the background classes combined spread (intra-class variance) may be minimal using a shape of a histogram of pixel intensities. The foreground/background separation procedure may leave salt and pepper noise in the resulting images, as seen in FIG. 5A. To reduce, remove, or otherwise eliminate the salt and pepper noise from the image, a baseline axis of the image may be removed, and a largest region of the Doppler image 20 may be retained. Large perceivable regions of the Doppler image 20 may be retained to ensure that a significant majority of the velocity profile is captured, as shown in FIG. 5B. Further, a morphological closing step may be applied to fill up small holes in the bright regions of the Doppler image 20 to yield an integrated velocity profile or Doppler image, as seen in FIG. 5C. Dilation may be used to fill up the holes in the largest region of the Doppler image 20. Then, the boundary pixels of the velocity profile may be traced to obtain the velocity envelope of the Doppler image 20, as shown in FIG. 5D. To extract a final velocity envelope, strong boundaries may be retained that are on either side of the baseline axis. As the baseline axis can be sometimes occluded by the measurement bars, measurement screens, or artifacts, simple image processing may not be sufficient to detect the baseline axis. An OCR engine may be utilized to find a velocity unit marker denoted by 'm/s' which can be positioned at the baseline axis line; the velocity unit marker may on a left side of the region of interest. For example, one or more templates may be created for the location containing the 'm/s' symbol and by template matching, the location may be isolated on the region of interest. In an exemplary embodiment, the y coordinate of the location of the velocity unit marker may then used as an estimate of the baseline axis. Finally, to remove an effect of spiking artifacts that may be embedded within the velocity signal, a temporal median filter may be utilized on the extracted envelopes.

Figure 6A:
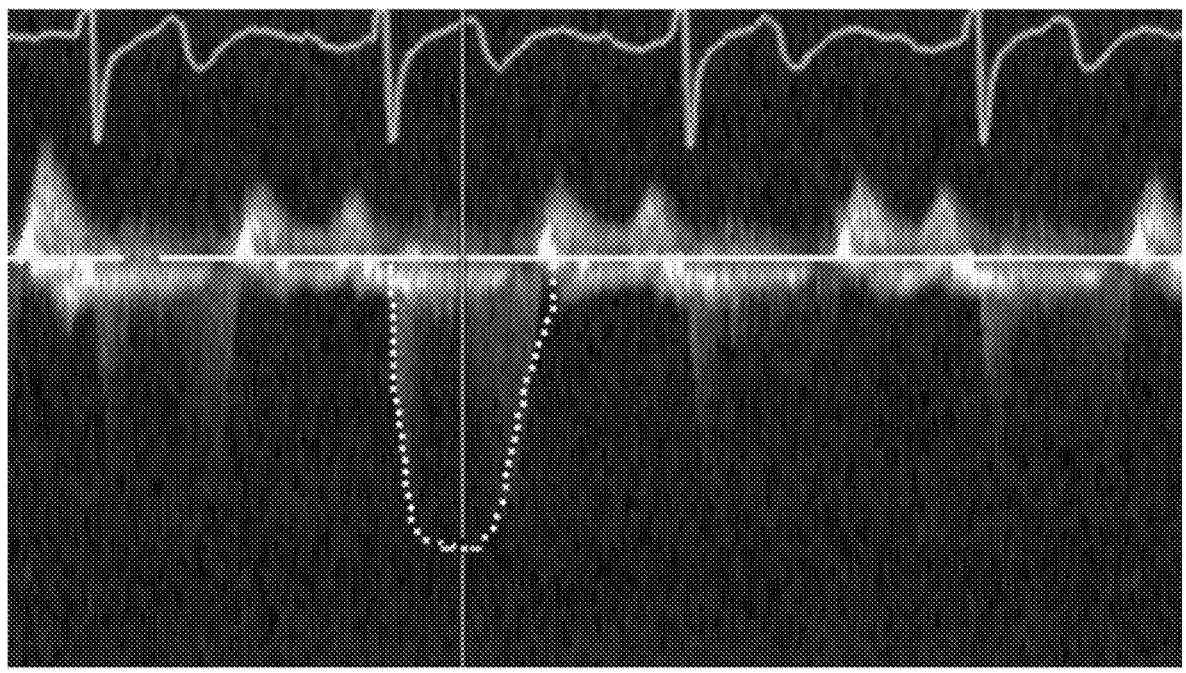
FIG. 6A depicts a Doppler image having an echocardiographer's delineation of a Doppler velocity region overlaid on the Doppler image, in accordance with embodiments of the present invention.
Figure 6B:
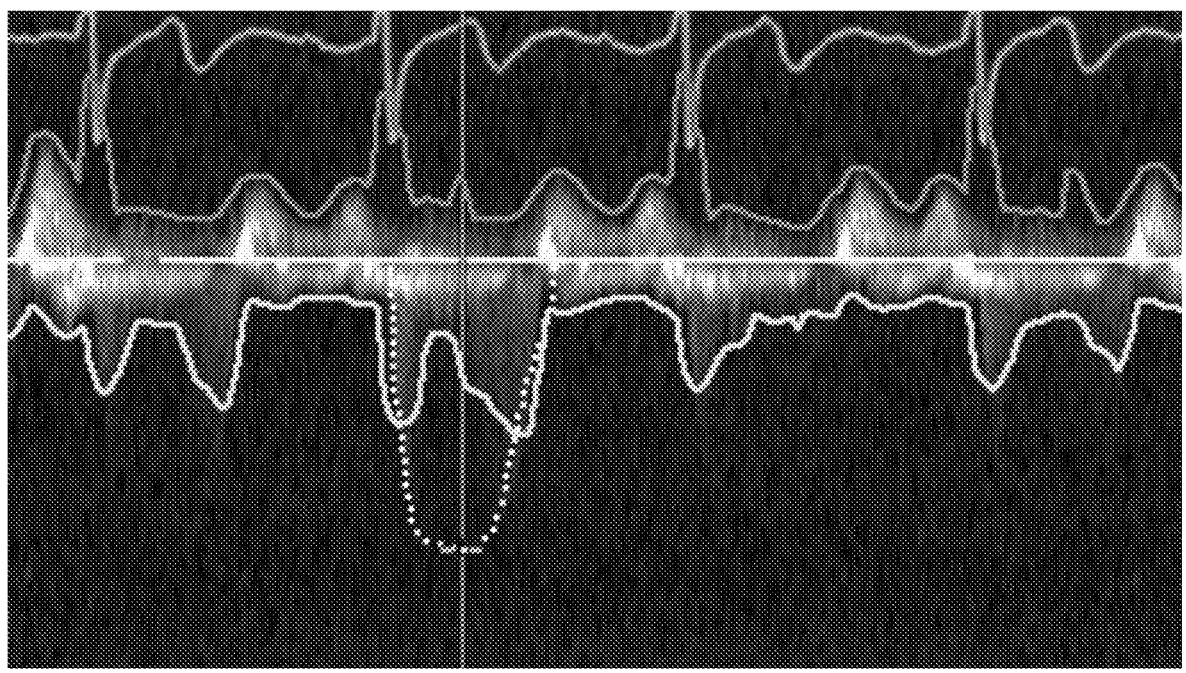
FIG. 6B depicts a Doppler image of an extracted velocity envelope without incorporation of a manually delineated envelope of FIG. 6A, in accordance with embodiments of the present invention.
Figure 6C:
FIG. 6C depicts a Doppler image having the extracted annotation added to the largest region of the Doppler image, in accordance with embodiments of the present invention.
Figure 6D:
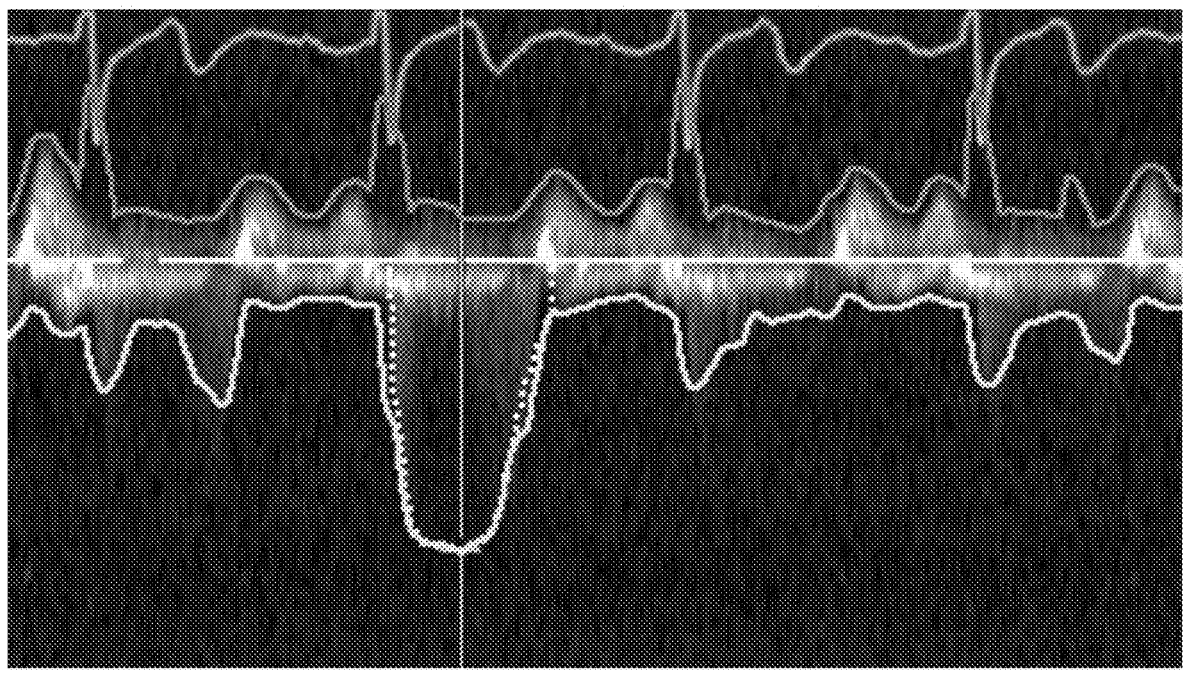
FIG. 6D depicts a Doppler image having an extracted velocity envelope, with incorporation of a manually delineated envelope, in accordance with embodiments of the present invention.

In some cases, such as images having faded curve boundary, the velocity envelop detection method may fail. In many such cases, however, clinician's annotation are available and could be extracted from these scans, as shown in FIGS. 6A-6D. In other words, embodiments of the method 100 may include extracting and incorporating a clinical annotation of the Doppler image 20 when the clinical annotation is present in the echocardiogram, to improve the velocity envelope. For most cases, echocardiographer's delineation of Doppler velocity region has been overlaid on echocardiogram images as seen for CW image of mitral valve in FIG. 6A. FIG. 6B depicts an extracted velocity envelope without incorporation of a manually delineated envelope. To extract the echocardiographer's annotation, the calculated Doppler velocity profile from the region of interest may be excluded, and Otsu's thresholding algorithm may be applied on the remaining image to highlight a manual delineation from a clinician, which may be connected to the baseline axis. Then, the extracted annotation may be added to the largest region of the Doppler image, as shown in FIG. 6C, and the boundary pixels may be extracted. Because most of the challenging images of the echocardiographer's annotation is available, the clinicians annotation may serve to improve the overall accuracy of the feature calculation. FIG. 6D depicts an embodiment of an extracted velocity envelope, with incorporation of a manually delineated envelope.

Figure 7:
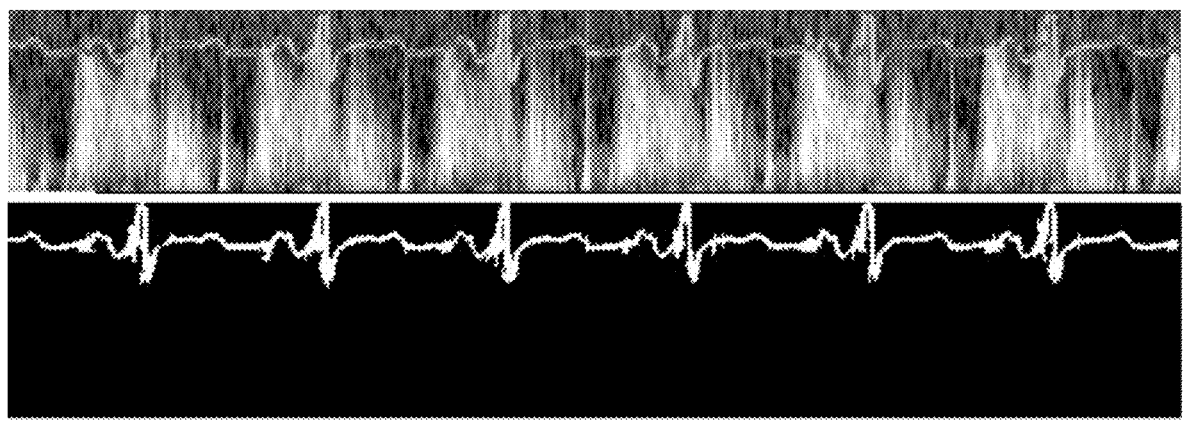
FIG. 7 depicts an extracted ECG signal from the region of interest, in accordance with embodiments of the present invention.

Referring back to FIG. 1, step 104 extracts the ECG signal 25 to synchronize the ECG signal 25 with the Doppler image 20 over the at least one heart cycle, within the region of interest. In other words, the ECG signal 25 may be synchronized with the Doppler image 20 within the region of interest, over at least one heart cycle, wherein the ECG signal is detected using a maximum energy function, as described below. In an exemplary embodiment, the ECG trace is recorded during Doppler imaging and appears along the top of the region of interest. A reliable method of ECG signal and ventricular systolic cycle detection can be important for clinical feature calculation and disease diagnosis. FIG. 7 depicts an extracted ECG signal from the region of interest. The ECG signal on the region of interest may be detected by solving an energy maximization problem. Because the ECG signal is a traversal from one side of the image to the opposite side, the ECG signal may be treated as a function of x, so that for each x, there is only one value of y. Thus, for an image of width N, the method attempts to find N values of y, such that the following salient properties are met: the ECG signal 1) is continuous, 2) has a consistent color profile, 3) is distinct from the background, 4) is not grayscale, while the rest of the image might or might not be so.

Based on the properties being met, an overall energy value may be assigned to each point, and the ECG detection problem can be posed as an energy maximization problem, finding the path that maximizes a cumulative sum of energy out of all the paths that traverse from left to the right. Each point (i,j) has this energy value:

$$E(i,j)=\lambda_1 E_{continuity}(i,j)+\lambda_2 E_{color}(i,j)+\lambda_3 E_{gradient}(i,j)+\lambda_4 E_{notgray}(i,j) \quad \text{(Eq. 1)}$$

In some embodiments, $\lambda_1$, $\lambda_2$, $\lambda_3$, and $\lambda_4$ may be calculated from the maximization of the total energy. Embodiments of $\lambda_1$, $\lambda_2$, $\lambda_3$, and $\lambda_4$ may be weighting factors that shows an importance of each term in final energy function. The values may be any real value between 0-1. $E_{continuity}$ refers to a continuity of the ECG signal, $E_{color}$ means a color of the ECG signal, $E_{gradient}$ refers to a gradient between the colors or intensity value of the ECG signal and the background, and $E_{notgray}$ refers to RGB values of the color of the ECG signal. Each energy term may define the ECG signal in comparison to the rest of the image.

The problem may be approached as a shortest path search problem, wherein a path from the source node on the left to the right side is to be found. This can be solved using Dijkstra's algorithm where for each node/point, only the neighboring points are relaxed while moving to the right. By sweeping k neighboring pixels for each Dijkstra relaxation step, the energy function in Eq. 1 are defined as follows:

$$E_{continuity} \propto 1/|j-k| \quad \text{(Eq. 2)}$$

rewards (e.g. energy term can be a higher number compared to the rest of image) if the distance between the successive path positions is small, $$E_{color} \propto \frac{1}{|I_r(i,j)-I_r(i+1,k)+I_g(i,j)-I_g(i+1,k)+I_b(i,j)-I_b(i+1,k)|} \quad \text{(Eq. 3)}$$

rewards (e.g. energy term can be a higher number compared to the rest of image) if values are close between successive path positions. Subscripts r, g, and b stand for red, green, and blue, respectively, $$E_{gradient} \propto |\nabla I(i,j)| \quad \text{(Eq. 4)}$$

rewards (e.g. energy term can be a higher number compared to the rest of image) if x and y gradients with respect to neighboring pixels are high, $$E_{notgray} \propto |I_r(i+1,k)-I_g(i+1,k)|+|I_b(i+1,k)-I_g(i+1,k)|+|I_b(i+1,k)-I_r(i+1,k)| \quad \text{(Eq. 5)}$$

rewards (e.g. energy term can be a higher number compared to the rest of image) if the pixels are not gray. Finally, we detect the QRS peaks of the extracted ECG by finding the maximum local arc-length of the curve and use the QRS peaks to synchronize the velocity envelops and the ECG signal.

Figure 8:
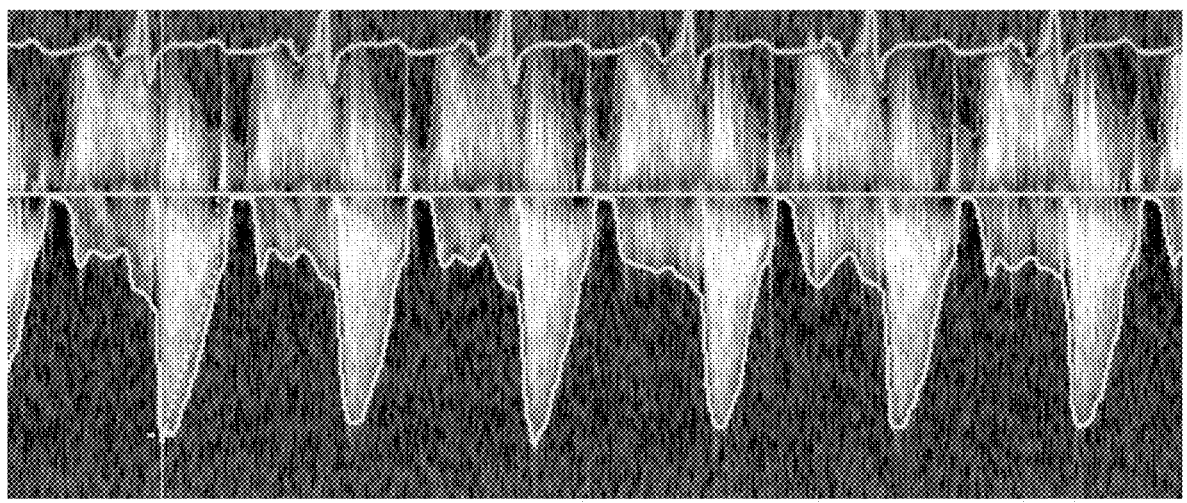
FIG. 8 depicts a Doppler image with the extracted ECG signal synchronized with the velocity envelope superimposed on the Doppler image, in accordance with embodiments of the present invention.
Figure 9A:
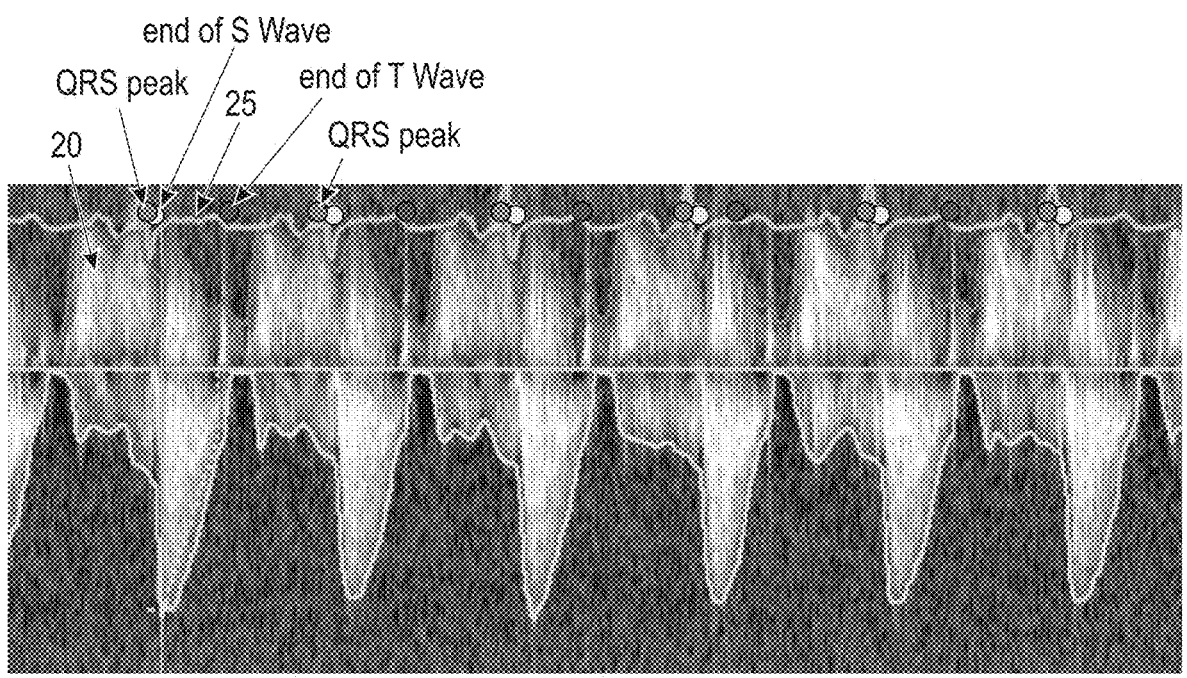
FIG. 9A depicts the Doppler image of FIG. 8, having QRS peaks, S wave and T wave ends labeled, in accordance with embodiments of the present invention.
Figure 9B:
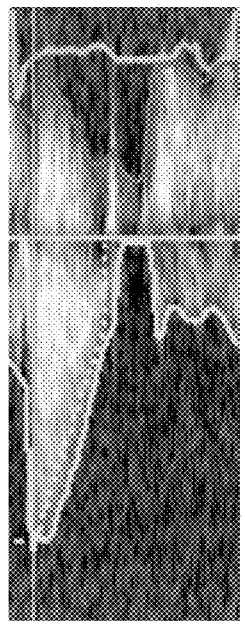
FIG. 9B depicts a cropped portion of the Doppler image of FIG. 9A, between two consecutive QRS peaks used for maximum velocity calculation, in accordance with embodiments of the present invention.
Figure 9C:
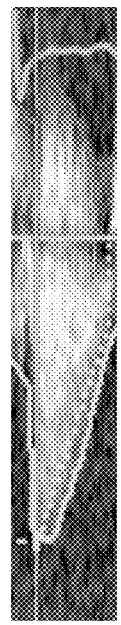
FIG. 9C depicts a cropped portion of the Doppler image of FIG. 9A, within a QT interval used for mean of pressure gradient calculation, in accordance with embodiments of the present invention.

Step 105 calculates a value of a clinical feature based on the extracted ECG signal synchronized with the velocity envelope that is superimposed on the Doppler image, which is depicted by FIGS. 8 and 9A. For instance, embodiments of the method 100 may determine at least one of a maximum jet velocity ($V_{max}$) and a mean pressure gradient (MPG) to diagnose a degree of a valvular disease of a patient. The clinical feature calculation from the extracted velocity envelope with the synchronized ECG signal may be superimposed on the Doppler image 20. A QRS peak, an end of the S wave, and an end of the T wave may be inserted onto the Doppler image for calculating clinical features. In one embodiment, a portion of the Doppler image and the velocity envelope superimposed onto the Doppler image may be cropped between two consecutive QRS peaks for maximum velocity calculation, as shown in FIG. 9B. In another embodiment, a portion of the Doppler image and the velocity envelope superimposed onto the Doppler image may be cropped within a QT interval for mean of pressure gradient calculation, as shown in FIG. 9C.

The maximum jet velocity may be determined by using an OCR reading of the values on the axes of the velocity profile. A value of velocity, in m/s, may be assigned to each point on the velocity envelope. A maximum value of velocity during systole within each cycle is a candidate for the $V_{max}$. One heart cycle of the data within the region of interest may be selected for reporting the $V_{max}$. A smart cycle selection pipeline may be used, which selects the heart cycle based on an existence of clinician annotation and maximum velocity among candidates.

The mean pressure gradient may be calculated from velocity information:

$$MPG \approx \Sigma 4V^2/n \quad \text{(Eq. 6)}$$

where n is the number of pixels within the QT interval, and V is the velocity, FIG. 4c. In some embodiments, V may be $V_m$, wherein $V_m$ is the velocity at pixel m, of total pixels n.

Referring again to FIG. 1, step 106 compares the values of the clinical features derived by step 105 with a clinical guideline for a particular disease. For example, the derived maximum velocity may be compared with a clinical guideline to determine a degree of a particular disease. The values may be compared with clinical guidelines to determine whether a patient's value are normal, moderate, severe, etc.

The following dataset is provided for exemplary purposes to show an embodiment of the implementation of method 100:

A set of 1479 CW Doppler images of an aortic valve area from 972 cardiac patients' echocardiogram video were collected from a large hospital network. Each echocardiogram study was associated with the text-only pages from the echocardiogram that reports diagnostic measurements as textual feature-value pairs, such as those shown in FIG. 1. To evaluate the results, two different sources were relied on: 1) echocardiogram video of each patient contains diagnostic measurements as textual feature-value pairs as seen in FIG. 1. Feature-value pairs were automatically extracted from embedded text in videos, and incorporated into the evaluation of the results; 2) for a subset of the available data, the reading of one clinician as a second opinion was obtained.

Figure 10A:
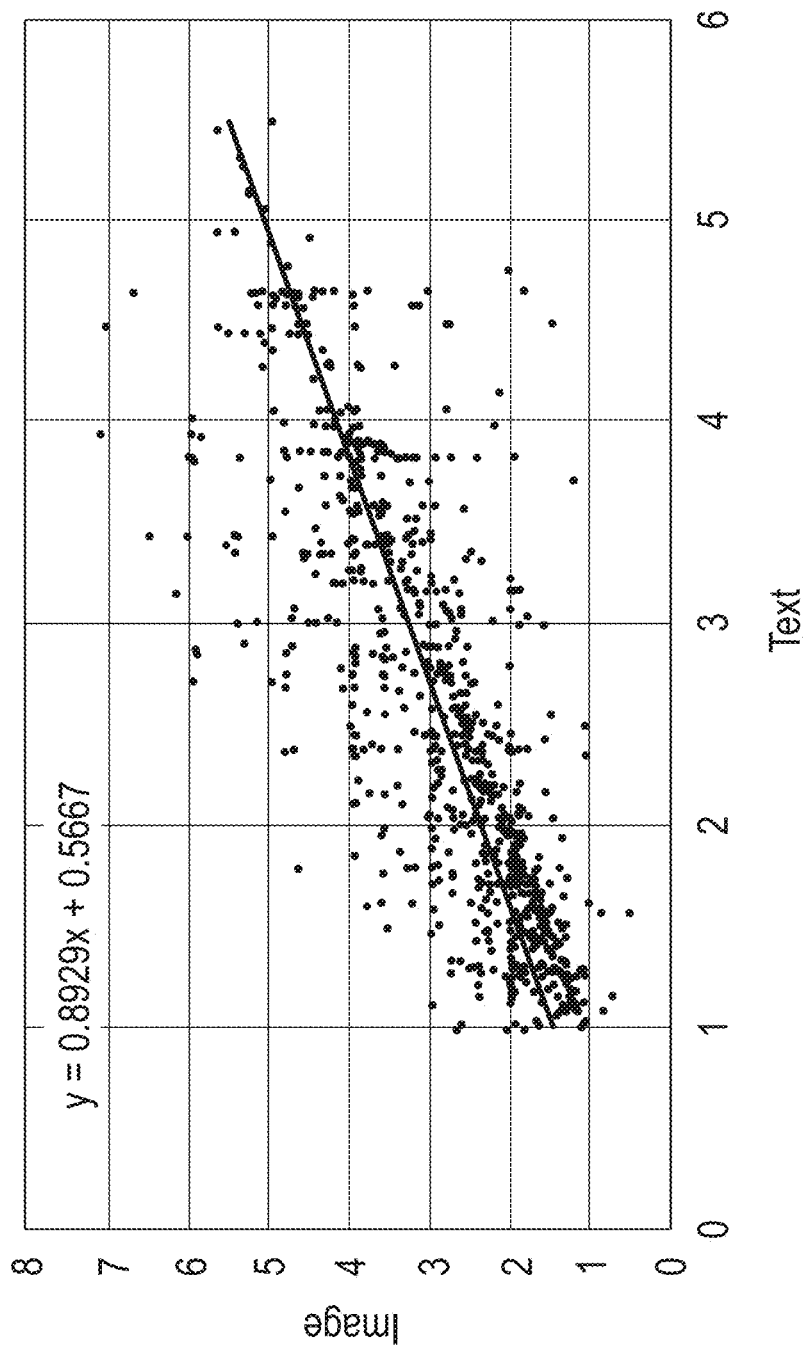
FIG. 10A depicts a graphical illustration of the relationship between the measurements from text frame and image, in accordance with embodiments of the present invention.
Figure 10B:
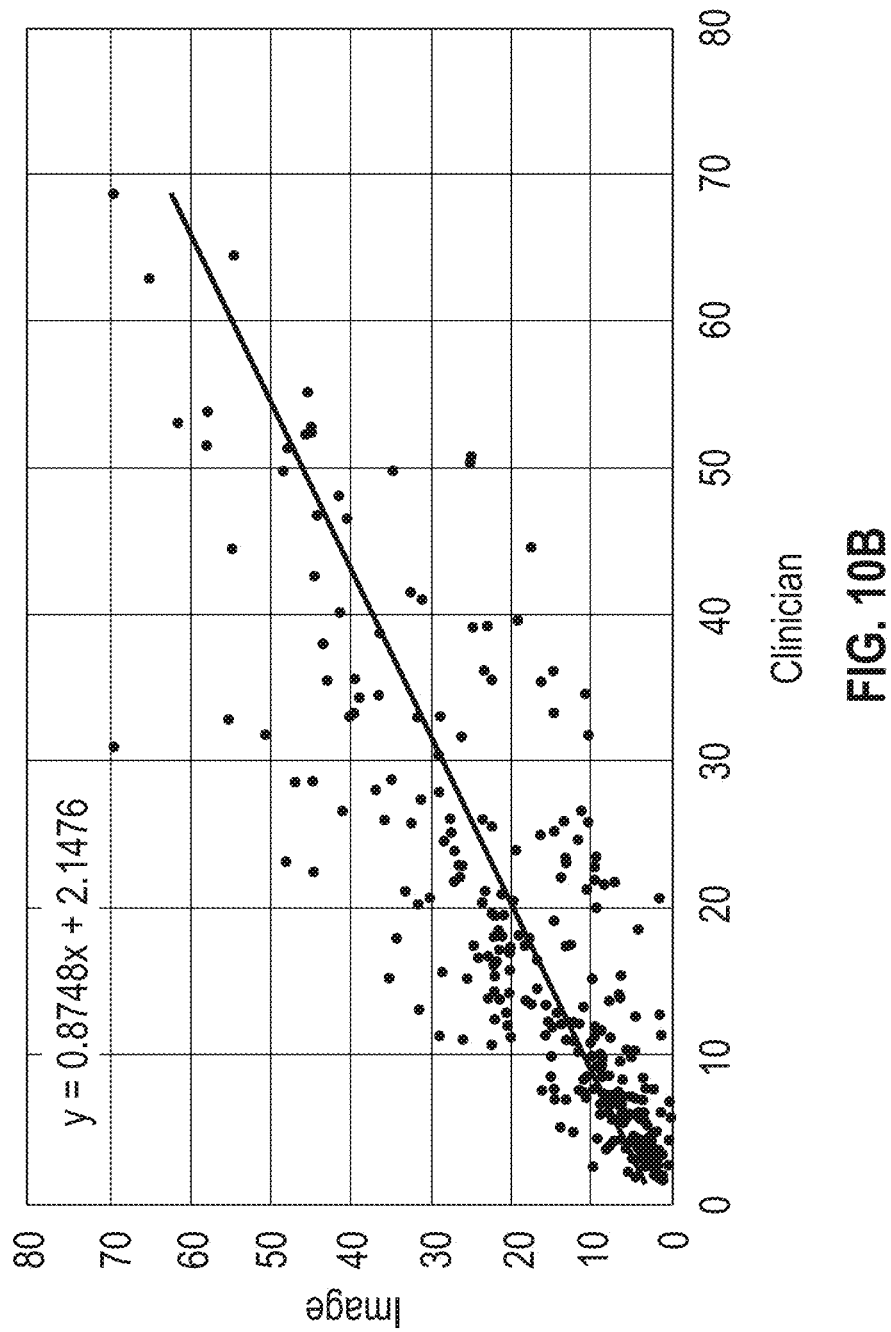
FIG. 10B depicts a graphical illustration of the calculated difference between the imaging-based and text-derived mean pressure gradient, in accordance with embodiments of the present invention.

Out of 1479 CW Doppler images, in case of 1054 images the value of $V_{max}$ was successfully extracted from the associated textual frames. The calculated difference between the imaging-based and text-derived $V_{max}$ is 0.29±0.78 m/s. FIG. 10A illustrates the relationship between the measurements from text frame and image. Similarly, for 785 CW Doppler images with associated text-based MPG measurements, the calculated difference between the imaging-based and text-derived MPG is 0.08±10.05 mmHg, as shown in FIG. 10B.

In addition, the second opinion expert measurement and recording of $V_{max}$ and MPG by a clinician was performed for 423 randomly selected CW Doppler images. The calculated difference between the imaging-based and clinician-measured $V_{max}$ is 0.39±0.78 m/s, as shown in FIG. 9C. For 318 CW Doppler images with clinician-recorded MPG measurements, the calculated difference is 0.12±7.93 mmHg (FIG. 5d).

To evaluate a performance of the proposed framework to find the patients with aortic stenosis, the calculated imaging-based $V_{max}$ and MPG were compared against the clinical thresholds for aortic stenosis. From 972 patients, 224 patients were detected with aortic stenosis based on the extracted measurements from textual frames, and 312 were detected with aortic stenosis with imaging-based measurements. Out of these 312 patients, 164 patients have been detected just by the imaging-based method. A clinician evaluated these 164 patients and confirmed that 92 of them were in fact positive for aortic stenosis. These would have been missed in the absence of the proposed image analytics pipeline described herein. Overall, embodiments of the method 100 shows a precision of 77% in aortic stenous detection based on measured $V_{max}$ and MPG.

Accordingly, embodiments of method 100 may be used for detection of the envelope of the velocity profile of the Doppler image while including and/or incorporating clinical annotations, which improves the overall accuracy of clinical feature extraction. Further, embodiments of method 100 extracts the ECG trace from the Doppler images to eventually derive the values of the critical clinical features from associated textual frames in echocardiogram videos, which can be used for validating the image-driven measurements and diagnosis. Based on a secondary clinical evaluation of all sources of available data, embodiments of method 100 results in at least a 9% increase in the true positive detection of aortic stenosis which represents an at risk population that can benefit from a follow-up.

Figure 11:
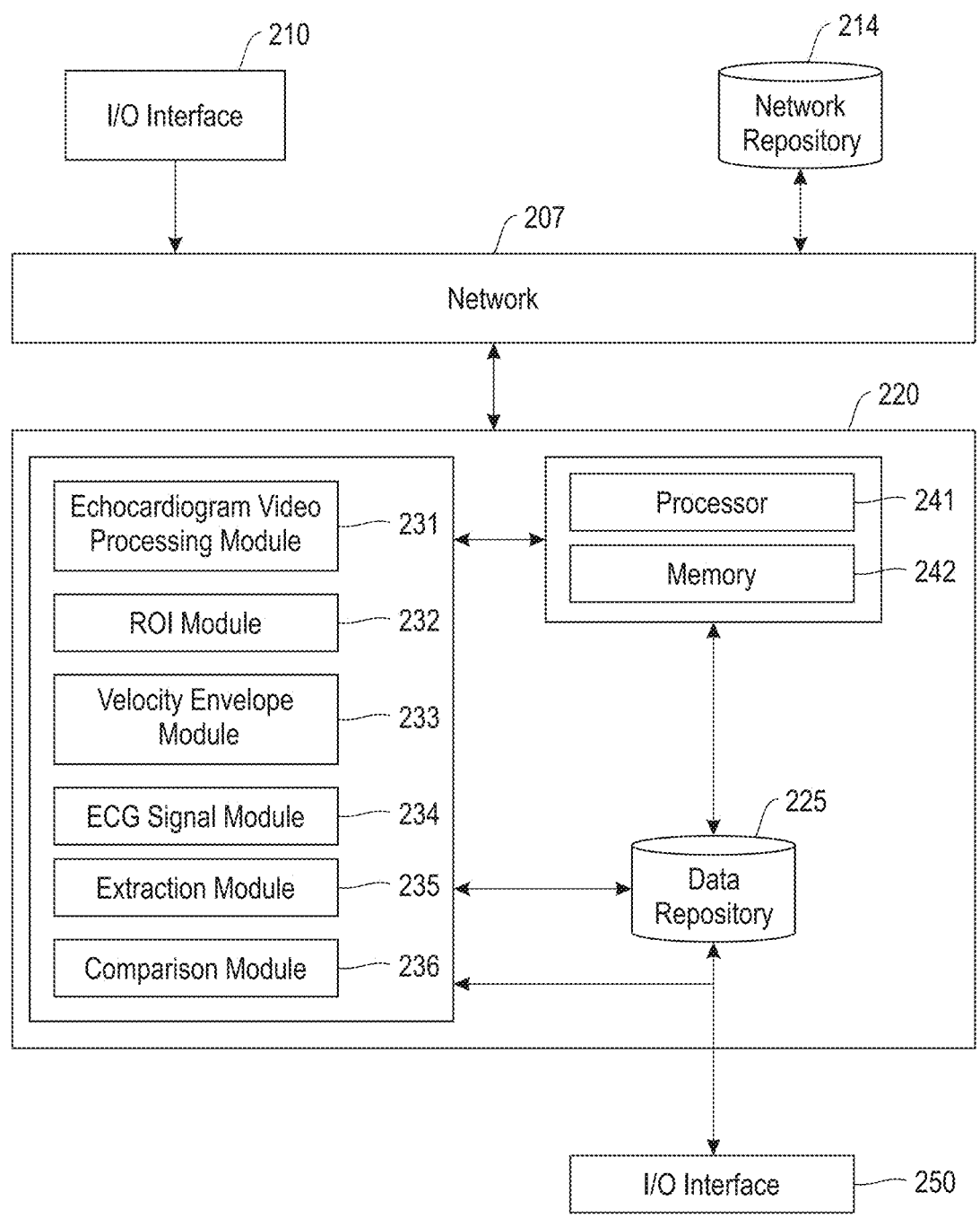
FIG. 11 depicts a block diagram of a clinical features extraction system, in accordance with embodiments of the present invention.

Referring now to FIG. 11, embodiments of method 100 may be an algorithm that may be implemented for automatic extraction of disease-specific features from Doppler images, in accordance with the flow chart described in FIG. 1, using one or more computer systems as defined generically in FIG. 12 below, and more specifically by the specific embodiments of FIG. 11 depicting a clinical feature extraction system 200.

Embodiment of clinical feature extraction system 200 may comprise one or more input/output interfaces, I/O device 210, 250 coupled to a computing system 220 either directly and/or over a network 207. A network 207 may refer to a group of two or more computer systems linked together. Network 207 may be any type of computer network known by individuals skilled in the art. Examples of computer networks 207 may include a LAN, WAN, campus area networks (CAN), home area networks (HAN), metropolitan area networks (MAN), an enterprise network, cloud computing network (either physical or virtual) e.g. the Internet, a cellular communication network such as GSM or CDMA network or a mobile communications data network. The architecture of the computer network 207 may be a peer-to-peer network in some embodiments, wherein in other embodiments, the network 207 may be organized as a client/server architecture.

An I/O interface 210, 250 may enable any communication process performed between the computer system 220 and the environment outside of the computer system 220. Input to the computing system 220 may enable the signals or instructions sent to the computing system 220, for example echocardiogram videos containing a series or a sequence of images, while output may enable the signals sent out from the computer system 220.

In some embodiments, the network 207 may further comprise, in addition to the computer system 220, a connection to one or more network accessible knowledge bases containing information of the user, network repositories 214 or other systems connected to the network 207 that may be considered nodes of the network 207. In some embodiments, where the computing system 220 or network repositories 214 allocate resources to be used by the other nodes of the network 207, the computer system 220 and network repository 214 may be referred to as servers.

The network repository 214 may be a data collection area on the network 207 which may back up and save all the data transmitted back and forth between the nodes of the network 207. For example, the network repository 214 may be a data center saving and cataloging results from echocardiograms administered to patients and analyzed by the method 100 to generate both historical and predictive reports regarding a particular patient. In some embodiments, a data collection center housing the network repository 214 may include an analytic module capable of analyzing each piece of data being stored by the network repository 214. Further, the computer system 220 may be integrated with or as a part of the data collection center housing the network repository 214. In some alternative embodiments, the network repository 214 may be a local repository (not shown) that is connected to the computer system 120.

Referring still to FIG. 11, embodiments of the computing system 220 may receive echocardiogram videos or a series of images via I/O interfaces 210, 250. Input devices or input mechanisms associated with the I/O interfaces 210, 250 may be an echocardiogram machine. Other embodiments of the I/O interfaces 210, 250 may be a touchscreen of a mobile device, one or more connected microphones, a keyboard, a webcam, mouse, touchpad, stylus, and the like, or other peripheral devices connected to the computing system 220 over the network 207 or via Bluetooth, IR, or other short range communication networks.

Embodiments of the computer system 220 may be equipped with a memory device 242 which may store patient results, and a processor 241 for implementing the tasks associated with the clinical feature extraction system 200.

Furthermore, embodiments of computer system 220 may an echocardiogram video processing module 231, a ROI module 232, a velocity envelope module 233. A ECG signal module 234, an extraction module 235, and a comparison module 236. A "module" may refer to a hardware based module, software based module or a module may be a combination of hardware and software. Embodiments of hardware based modules may include self-contained components such as chipsets, specialized circuitry and one or more memory devices, while a software-based module may be part of a program code or linked to the program code containing specific programmed instructions, which may be loaded in the memory device of the computer system 220. A module (whether hardware, software, or a combination thereof) may be designed to implement or execute one or more particular functions or routines.

Embodiments of the echocardiogram video processing module 231 may include one or more components of hardware and/or software program code for obtaining a raw Doppler image from a series of images of an echocardiogram video, the series of images being received from an echocardiogram machine either wirelessly over network 207, or directly via I/O interface 250. The echocardiogram video processing module 231 may communicate with the echocardiogram machine to receive the series of images of the echocardiogram, and may obtain a raw Doppler image from the series of images, as described supra. Embodiments of the computing system 220 may further include a region of interest (ROI) module 232. Embodiments of the ROI module 232 may include one or more components of hardware and/or software program code for isolating a region of interest from the raw Doppler image. The ROI module 232 may apply various foreground/background separation techniques to remove unwanted elements of the raw Doppler image, resulting in a region of interest including a ECG signal and Doppler image, as described above. Embodiments of the computing system 220 may also include a velocity envelope module 233. Embodiments of the velocity envelope module 233 may include one or more components of hardware and/or software program code for determining a velocity envelope of the Doppler image within the region of interest, as described in greater detail above. Embodiments of the computing system 220 may include an ECG signal module 234. Embodiments of the ECG signal module 234 may include one or more components of hardware and/or software program code for extracting the ECG signal to synchronize the ECG signal with the Doppler image over the at least one heart cycle, within the region of interest, as described in greater detail above. Embodiments of the computing system 220 may include an extraction module 235. Embodiments of the extraction module 235 may include one or more components of hardware and/or software program code for calculating a value of a clinical feature based on the extracted ECG signal synchronized with the velocity envelope that is superimposed on the Doppler image, as described in greater detail above. Embodiments of the computing system 220 may further include a comparison module 236. Embodiments of the comparison module 236 may include one or more components of hardware and/or software program code for comparing the value of the clinical feature with clinical guidelines associated with the clinical feature to determine a diagnosis of a disease, as described in greater detail above.

Various tasks and specific functions of the modules of the computing system 220 may be performed by additional modules, or may be combined into other module(s) to reduce the number of modules. Further, embodiments of the computer or computer system 220 may comprise specialized, non-generic hardware and circuitry (i.e., specialized discrete non-generic analog, digital, and logic based circuitry) for (independently or in combination) particularized for executing the methods in accordance with the present invention. The specialized discrete non-generic analog, digital, and logic based circuitry may include proprietary specially designed components (e.g., a specialized integrated circuit, such as for example an Application Specific Integrated Circuit (ASIC), designed for only implementing methods of the present invention). Moreover, embodiments of the clinical feature extraction system 200 may improve a detecting of valvular diseases, especially in comparison with manual delineations of velocity profiles.

Figure 12:
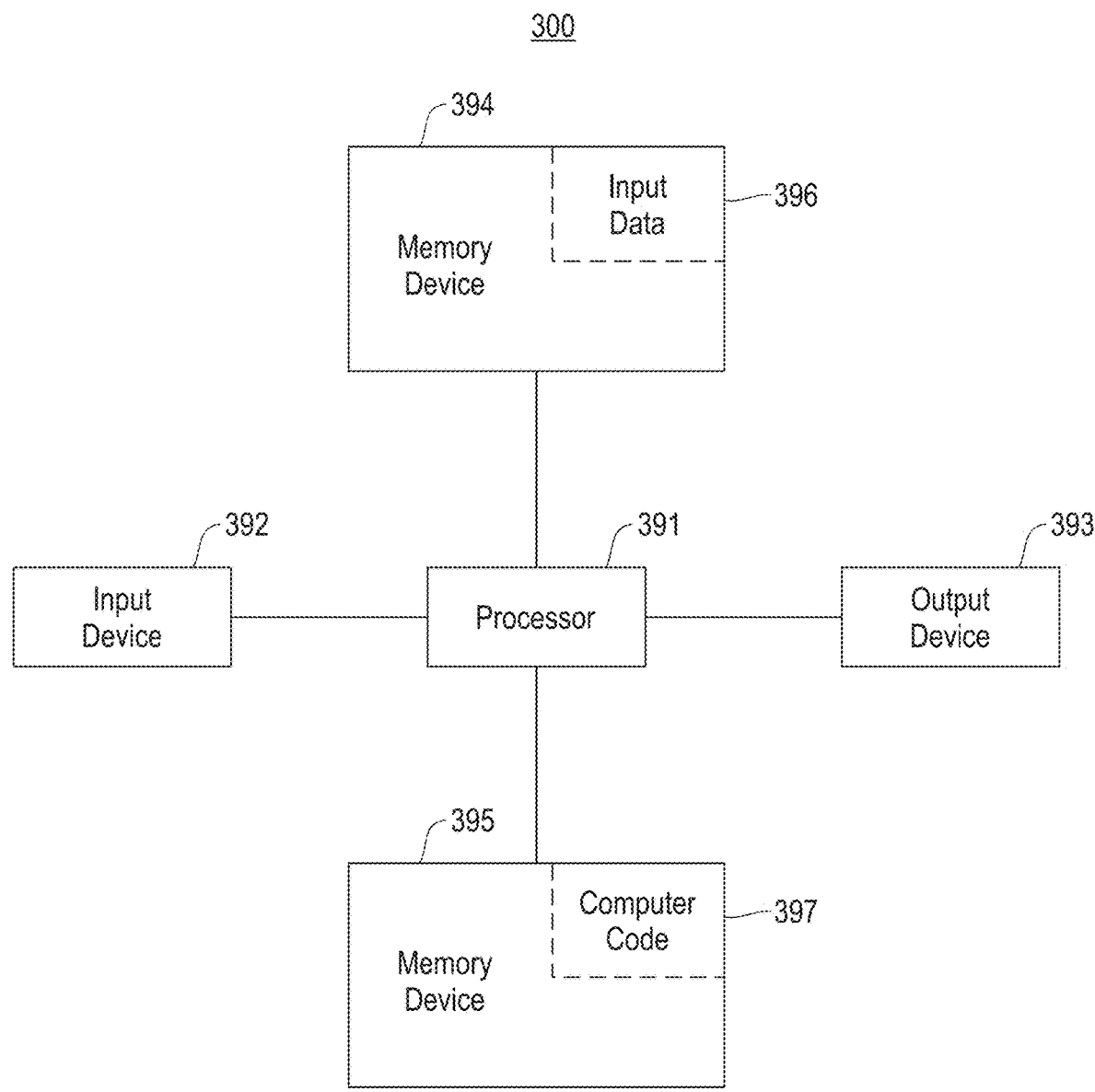
FIG. 12 illustrates a block diagram of a computer system for the clinical features extraction system of FIG. 11, capable of implementing methods for automatically detecting disease-specific features using Doppler images of FIG. 2, in accordance with embodiments of the present invention.

FIG. 12 illustrates a block diagram of a computer system 300 that may be included in the system of FIG. 11 and for implementing the methods of FIG. 2 in accordance with the embodiments of the present disclosure. The computer system 300 may generally comprise a processor 5391, an input device 392 coupled to the processor 391, an output device 393 coupled to the processor 391, and memory devices 394 and 395 each coupled to the processor 391. The input device 392, output device 393 and memory devices 394, 395 may each be coupled to the processor 391 via a bus. Processor 391 may perform computations and control the functions of computer 300, including executing instructions included in the computer code 397 for the tools and programs capable of implementing a method for automatic extraction of disease-specific features from Doppler images, in the manner prescribed by the embodiments of FIGS. 2-10B using the clinical feature extraction system of FIG. 11, wherein the instructions of the computer code 397 may be executed by processor 391 via memory device 395. The computer code 397 may include software or program instructions that may implement one or more algorithms for implementing the methods for automatic extraction of disease-specific features from Doppler images, as described in detail above. The processor 391 executes the computer code 397. Processor 391 may include a single processing unit, or may be distributed across one or more processing units in one or more locations (e.g., on a client and server).

The memory device 394 may include input data 396. The input data 396 includes any inputs required by the computer code 397. The output device 393 displays output from the computer code 397. Either or both memory devices 394 and 395 may be used as a computer usable storage medium (or program storage device) having a computer readable program embodied therein and/or having other data stored therein, wherein the computer readable program comprises the computer code 397. Generally, a computer program product (or, alternatively, an article of manufacture) of the computer system 300 may comprise said computer usable storage medium (or said program storage device).

Memory devices 394, 395 include any known computer readable storage medium, including those described in detail below. In one embodiment, cache memory elements of memory devices 394, 395 may provide temporary storage of at least some program code (e.g., computer code 397) in order to reduce the number of times code must be retrieved from bulk storage while instructions of the computer code 397 are executed. Moreover, similar to processor 391, memory devices 394, 395 may reside at a single physical location, including one or more types of data storage, or be distributed across a plurality of physical systems in various forms. Further, memory devices 394, 395 can include data distributed across, for example, a local area network (LAN) or a wide area network (WAN). Further, memory devices 394, 395 may include an operating system (not shown) and may include other systems not shown in FIG. 11.

In some embodiments, the computer system 300 may further be coupled to an Input/output (I/O) interface and a computer data storage unit. An I/O interface may include any system for exchanging information to or from an input device 392 or output device 393. The input device 392 may be, inter alia, a keyboard, a mouse, etc. or in some embodiments an echocardiogram machine. The output device 393 may be, inter alia, a printer, a plotter, a display device (such as a computer screen), a magnetic tape, a removable hard disk, a floppy disk, etc. The memory devices 394 and 395 may be, inter alia, a hard disk, a floppy disk, a magnetic tape, an optical storage such as a compact disc (CD) or a digital video disc (DVD), a dynamic random access memory (DRAM), a read-only memory (ROM), etc. The bus may provide a communication link between each of the components in computer 300, and may include any type of transmission link, including electrical, optical, wireless, etc.

An I/O interface may allow computer system 300 to store information (e.g., data or program instructions such as program code 397) on and retrieve the information from computer data storage unit (not shown). Computer data storage unit includes a known computer-readable storage medium, which is described below. In one embodiment, computer data storage unit may be a non-volatile data storage device, such as a magnetic disk drive (i.e., hard disk drive) or an optical disc drive (e.g., a CD-ROM drive which receives a CD-ROM disk). In other embodiments, the data storage unit may include a knowledge base or data repository 225 as shown in FIG. 11.

As will be appreciated by one skilled in the art, in a first embodiment, the present invention may be a method; in a second embodiment, the present invention may be a system; and in a third embodiment, the present invention may be a computer program product. Any of the components of the embodiments of the present invention can be deployed, managed, serviced, etc. by a service provider that offers to deploy or integrate computing infrastructure with respect to calendar processing systems and methods. Thus, an embodiment of the present invention discloses a process for supporting computer infrastructure, where the process includes providing at least one support service for at least one of integrating, hosting, maintaining and deploying computer-readable code (e.g., program code 397) in a computer system (e.g., computer 300) including one or more processor(s) 391, wherein the processor(s) carry out instructions contained in the computer code 397 causing the computer system to extract disease-specific features from Doppler images. Another embodiment discloses a process for supporting computer infrastructure, where the process includes integrating computer-readable program code into a computer system including a processor.

The step of integrating includes storing the program code in a computer-readable storage device of the computer system through use of the processor. The program code, upon being executed by the processor, implements a method of processing application permissions. Thus, the present invention discloses a process for supporting, deploying and/or integrating computer infrastructure, integrating, hosting, maintaining, and deploying computer-readable code into the computer system 300, wherein the code in combination with the computer system 300 is capable of performing a method for automatic extraction of disease-specific features from Doppler images.

A computer program product of the present invention comprises one or more computer readable hardware storage devices having computer readable program code stored therein, said program code containing instructions executable by one or more processors of a computer system to implement the methods of the present invention.

A computer system of the present invention comprises one or more processors, one or more memories, and one or more computer readable hardware storage devices, said one or more hardware storage devices containing program code executable by the one or more processors via the one or more memories to implement the methods of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for automatic extraction of disease-specific features from Doppler images, comprising:
    obtaining a raw Doppler image from a series of images of an echocardiogram;
    isolating a region of interest from the raw Doppler image, the region of interest (i) including a Doppler image and an ECG signal, and (ii) depicting at least one heart cycle;
    determining a velocity envelope of the Doppler image in the region of interest;
    extracting the ECG signal, and synchronizing the extracted ECG signal with the Doppler image over the at least one heart cycle, within the region of interest;
    calculating a value of a clinical feature based on the extracted ECG signal synchronized with the velocity envelope, wherein a portion of the Doppler image and the velocity envelope superimposed on the Doppler image is cropped:
    between two QRS peaks for calculating a maximum jet velocity, and
    within a QT interval for calculating a mean pressure gradient, wherein the mean pressure gradient (MPG) is calculated from:

$$MPG \approx \Sigma 4V^2/n$$

where n is a number of pixels within the QT interval, and V is the velocity; and
    comparing the value of the clinical feature with clinical guidelines associated with the clinical feature to determine a diagnosis of a disease.

2. The method of claim 1, wherein the obtaining the raw Doppler image includes categorizing the series of images using optical character recognition and machine learning.

3. The method of claim 1, wherein the determining the velocity envelope includes tracing the Doppler image after applying a foreground/background separation technique.

4. The method of claim 1, wherein the extracting the ECG signal includes detecting the ECG signal using an energy maximization equation.

5. The method of claim 4, wherein the energy maximization equation is:
    $E(i,j)=\lambda_1 E_{continuity}(i,j)+\lambda_2 E_{color}(i,j)+\lambda_3 E_{gradient}(i,j)+\lambda_4 E_{notgray}(i,j)$ wherein $E(i,j)$ is an energy value, $E_{continuity}(i,j)$ is a continuity of the ECG signal, $E_{color}(i,j)$ is a color profile of the ECG signal, $E_{gradient}(i,j)$ is a gradient between the color profile of the ECG signal and a background of the image, $E_{notgray}(i,j)$ is RGB value of the ECG signal that is not gray, and each of, $\lambda_1$, $\lambda_2$, $\lambda_3$, and $\lambda_4$ is a weighting factor.

6. The method of claim 1, further comprising:
    extracting a clinical annotation of the Doppler image when the clinical annotation is present in the echocardiogram, and incorporating the clinical annotation when determining the velocity envelope.

7. The method of claim 1, wherein the velocity envelope includes an upper envelop associated with a positive velocity value.

8. The method of claim 1, wherein the velocity envelope includes a lower envelop associated with a negative velocity value.

9. The method of claim 1, wherein the raw Doppler image is at least one of a continuous wave (CW) Doppler image and a pulse wave (PW) Doppler image.

10. The method of claim 1, wherein the disease is aortic stenosis.

11. A method for deriving a clinical feature from Doppler images to diagnose a valvular disease, comprising:
    tracing a Doppler image located within a region of interest to extract an upper velocity envelope and a lower velocity envelope of the Doppler image, wherein the region of interest is created from a raw Doppler image, the raw Doppler image being obtained from a series of images of an echocardiogram;
    synchronizing an ECG signal with the Doppler image within the region of interest, over at least one heart cycle, the ECG signal being detecting using a maximum energy function; and
    determining at least one of a maximum jet velocity and a mean pressure gradient to diagnose the valvular disease of a patient, wherein a portion of the Doppler image and the velocity envelope superimposed on the Doppler image is cropped:
    between two QRS peaks for calculating the maximum jet velocity, and
    within a QT interval for calculating the mean pressure gradient, wherein the mean pressure gradient (MPG) is calculated from:

$$MPG \approx \Sigma 4V^2/n$$

where n is a number of pixels within the QT interval, and V is the velocity.

12. The method of claim 11, wherein the ECG signal is detected using an energy maximization equation.

13. The method of claim 12, wherein the energy maximization equation is:
    $E(i,j)\lambda_1 E_{continuity}(i,j)+\lambda_2 E_{color}(i,j)+\lambda_3 E_{gradient}(i,j)+\lambda_4 E_{notgray}(i,j)$ wherein $E(i,j)$ is an energy value, $E_{continuity}(i,j)$ is a continuity of the ECG signal, $E_{color}(i,j)$ is a color profile of the ECG signal, $E_{gradient}(i,j)$ is a gradient between the color profile of the ECG signal and a background of the image, $E_{notgray}(i,j)$ is RGB value of the ECG signal that is not gray, and each of, $\lambda_1$, $\lambda_2$, $\lambda_3$, and $\lambda_4$ is a weighting factor.

14. The method of claim 11, further comprising:
    extracting and incorporating a clinical annotation of the Doppler image when the clinical annotation is present in the echocardiogram.

15. A method for automatic extraction of disease-specific features from Doppler images, comprising:
    obtaining, by a processor of a computing system, a raw Doppler image from a series of images of an echocardiogram, received from an echocardiogram machine;
    isolating, by the processor, a region of interest from the raw Doppler image, the region of interest including a Doppler image and an ECG signal over at least one heart cycle;
    determining, by the processor, a velocity envelope of the Doppler image in the region of interest;
    synchronizing, by the processor, the ECG signal with the Doppler image over the at least one heart cycle, within the region of interest;
    calculating, by the processor, a value of a clinical feature from the ECG signal superimposed on the Doppler image, wherein a portion of the Doppler image and the velocity envelope superimposed on the Doppler image is cropped:
between two QRS peaks for calculating a maximum jet velocity, and
within a QT interval for calculating a mean pressure gradient, wherein the mean pressure gradient (MPG) is calculated from:

$$MPG \approx \Sigma 4V^2/n$$

where n is a number of pixels within the QT interval, and V is the velocity; and
comparing, by the processor, the value of the clinical feature with clinical guidelines associated with the clinical feature to determine a diagnosis of a disease.

16. The method of claim 15, wherein the obtaining the raw Doppler image includes categorizing the series of images using optical character recognition and machine learning.

17. The method of claim 15, wherein the extracting the ECG signal includes detecting the ECG signal using an energy maximization equation, the energy maximization equation being: $E(i,j)=\lambda_1 E_{continuity}(i,j)+\lambda_2 E_{color}(i,j)+\lambda_3 E_{gradient}(i,j)+\lambda_4 E_{notgray}(i,j)$ wherein $E(i,j)$ is an energy value, $E_{continuity}(i,j)$ is a continuity of the ECG signal, $E_{color}(i,j)$ is a color profile of the ECG signal, $E_{gradient}(i,j)$ is a gradient between the color profile of the ECG signal and a background of the image, $E_{notgray}(i,j)$ is RGB value of the ECG signal that is not gray, and each of, $\lambda_1, \lambda_2, \lambda_3$, and $\lambda_4$ is a weighting factor.

18. The method of claim 15, further comprising:
extracting a clinical annotation of the Doppler image when the clinical annotation is present in the echocardiogram, and incorporating the clinical annotation when determining the velocity envelope.

* * * * *